United States Patent [19]

Bare

[11] 4,401,356
[45] Aug. 30, 1983

[54] ELECTRICAL TERMINAL

[75] Inventor: Rex O. Bare, Lawrence, Kans.

[73] Assignee: C. R. Bard, Inc., Murray Hill, N.J.

[21] Appl. No.: 209,543

[22] Filed: Nov. 24, 1980

[51] Int. Cl.³ .............................................. H01R 11/22
[52] U.S. Cl. ................................ 339/258 R; 128/639; 339/17 F; 339/176 MF
[58] Field of Search .............. 339/74 R, 17 L, 17 LC, 339/17 C, 253 R, 258 R, 258 P, 258 S, 17 F, 256 SP, 261, 176 MF; 128/639–641, 644

[56] References Cited

U.S. PATENT DOCUMENTS

| | | | |
|---|---|---|---|
| 2,794,963 | 6/1957 | Hess et al. | 339/258 |
| 2,928,063 | 3/1960 | Gammel, Sr. | 339/17 |
| 3,030,603 | 4/1962 | Olsson | 339/258 S X |
| 3,140,907 | 7/1964 | Davies | 339/17 |
| 3,200,360 | 8/1965 | McKiel | 339/17 |
| 3,417,362 | 12/1968 | Reynolds | 339/17 |
| 3,550,067 | 12/1970 | Hansen | 339/217 |
| 3,720,209 | 3/1973 | Bolduc | 128/2.06 |
| 3,729,701 | 4/1973 | Smith | 339/223 |
| 3,858,152 | 12/1974 | Cowsert | 339/17 |
| 3,864,007 | 2/1975 | Plyler et al. | 339/17 |
| 3,945,710 | 3/1976 | Gartland | 339/258 R |
| 4,018,495 | 4/1977 | Freitag | 339/17 |
| 4,050,453 | 9/1977 | Castillo et al. | 128/206 E |
| 4,175,821 | 11/1979 | Hunter | 339/258 R |

*Primary Examiner*—Joseph H. McGlynn
*Attorney, Agent, or Firm*—Trexler, Bushnell & Wolters, Ltd.

[57] ABSTRACT

An electrical terminal for making conductive connection with a printed circuit conductor on one side of a dielectric sheet comprises a wiper section adapted to make contact with the printed circuit conductor and a blade section adapted to make contact with the opposite side of the sheet, the wiper section being struck from the blade section but leaving a part of the wiper section within the perimeter of the strike out opening so that upon insertion of the sheet between the blade and wiper sections, those sections spread apart and apply opposed clamping pressure to opposite sides of the sheet. The terminals are intended to provide electrical connections between a wiring harness and skin contact electrodes for measuring physiologic functions.

3 Claims, 7 Drawing Figures

ELECTRICAL TERMINAL

BACKGROUND OF THE INVENTION

This invention relates to electrical terminals, and more particularly to a terminal for making electrically conductive contact with a printed electric circuit conductor on a thin flexible sheet of dielectric material.

The terminal of the present invention was developed primarily for use with a skin contact electrode of the type used for measuring physiologic functions, for instance in electrocardiography and electroencephalography. Electrodes of the foregoing type may be of an individual nature, or manufactured in clusters which are attached to a thin foam rubber pad. The electrodes are in a series of spaced locations on the pad and are connected by lead wires to monitoring equipment, such as the electrocardiograph. In certain medical procedures involving the chest area, such as lung or abdominal surgery, it is not practical to monitor the patient via the chest area, and the electrode cluster is affixed to the back of the patient. This necessitates that the patient lie upon the cluster, or "back-pad" as it is often referred to, both during surgery and thereafter during the recovery period. As the recovery period may be extensive, the question of patient comfort becomes significant, and the relative size, i.e. most particularly the bulk or height of the terminal connector used to make contact between the lead wires and the electrode assembly or back-pad is key factor in patient comfort or discomfort. In the prior art various terminals may be found which are of a "high profile" nature. These terminals are relatively deep or thick as compared to the thickness of the pad. These high profile terminals may tend to be bothersome and uncomfortable for the patient. Another type of prior art terminal is of a "low profile" type. This type of terminal is welded to the electrode or to the electrode lead. The welded connections, however, tend to increase the cost of the back pad.

OBJECTS AND SUMMARY OF THE INVENTION

An object of the present invention is to provide a low profile electrical terminal which is readily connected to a printed circuit electrical conductor on a sheet of dielectric material, which sheet also contains the electrodes and constitutes a part of the back pad.

A further object of this invention is to provide a low profile terminal of the type stated which firmly grips a printed electrical circuit conductor, constituting the lead from the terminal to an electrode.

In accordance with the foregoing objects, the invention comprises a terminal for making electrically conductive connection with a printed circuit electrical conductor on one side of a thin flexible sheet of dielectric material, said terminal comprising a resilient electrically conductive body having first and second opposite ends, said first end having attaching means for connection to an electrical conductor, said body having a blade section and wiper section, the wiper section being struck from the blade section along a U-shape line but remaining joined thereto at a region adjacent to said attaching means, said wiper section and said blade section being bent to form portions that diverge in the direction toward said second end to receive the dielectric sheet such that the wiper section is a wiping contact that is adapted to engage the printed conductor and the blade section is adapted to engage the sheet on the side thereof opposite to said printed conductor, said wiper section and blade sections having adjacent sheet-engaging parts that are spaced such that insertion of the dielectric sheet between said parts spreads the wiper and blade sections causing the wiper and blade sections to apply opposed gripping forces to the sheet on opposite sides thereof, and means on said body adapted to cooperate with a perforation in said sheet for inhibiting relative sliding movement of the sheet and said body.

DETAILED DESCRIPTION OF THE ILLUSTRATION EMBODIMENT

Figure 1:
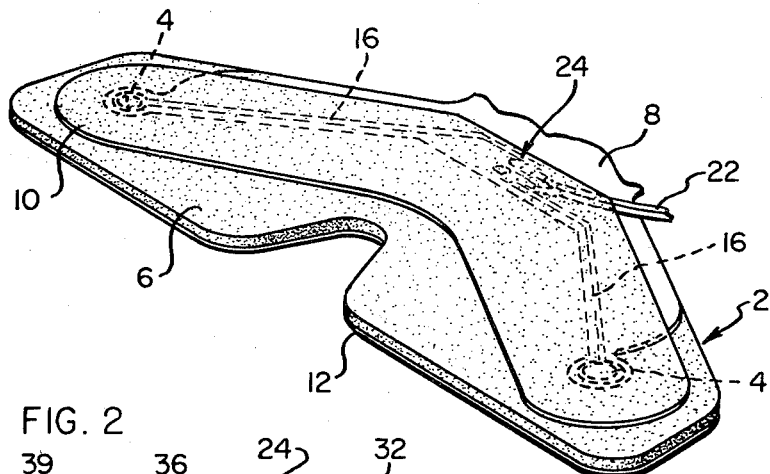
FIG. 1 is a fragmentary perspective view of a portion of a back-pad containing a terminal constructed in accordance with and embodying the present invention.

Referring now in more detail to the drawings, there is shown in FIG. 1, a portion of a back-pad 2 that contains a skin contact electrode cluster for use in electrocardiography or the like. A fragmentary portion of the back-pad 2 is shown including two electrodes 4,4 which typically may include gel pads of conventional construction. Essentially, one-half of the back-pad is shown in FIG. 1, it being understood that the opposite half is of like construction. The back-pad 2 includes a foam sheet 6, a dielectric plastic sheet 8, that is much thinner than the sheet 6, and a second thinner foam sheet 10, and a release liner 12. The foam sheet 6 has holes in the regions of the electrodes 4,4 for receiving the gel pads. The foam sheet 6 also is covered with pressure sensitive adhesive on its outwardly presented surface and which is covered by the release liner 12. The release liner 12 is stripped from the back-pad just prior to use of the unit. On the inwardly presented surface of the thinner foam sheet 10 is a band of adhesive for securing the thinner foam sheet 10 to the foam sheet 6. The foam sheets 6 and 10 may be made of a polyethylene foam.

The flexible dielectric sheet 8 may be fabricated of a polyethylene terephthalate resin of the type sold under the trademark "Mylar" and having a thickness of about 0.004 inches. The dielectric sheet 8 has the electrodes printed on one side thereof as well as a printed conductor 16 (typically of silver ink) running from each electrode 4. The printed conductors 16 (in this instance there are four of them) extend to approximately the middle of the pad and terminate in short transverse line segments 18 shown disposed in two adjacent pairs. The conductive line segments 18 are connected through terminals of the present invention to a wiring harness 20 which, in turn, provides electrical connections from the electrodes to the electrocardiograph or monitoring equipment, as the case may be. A more detailed description of the construction of the back pad 2 may be found in my co-pending application Ser. No. 100,904, filed Dec. 6, 1979, which disclosure is incorporated herein by reference.

Figure 2:
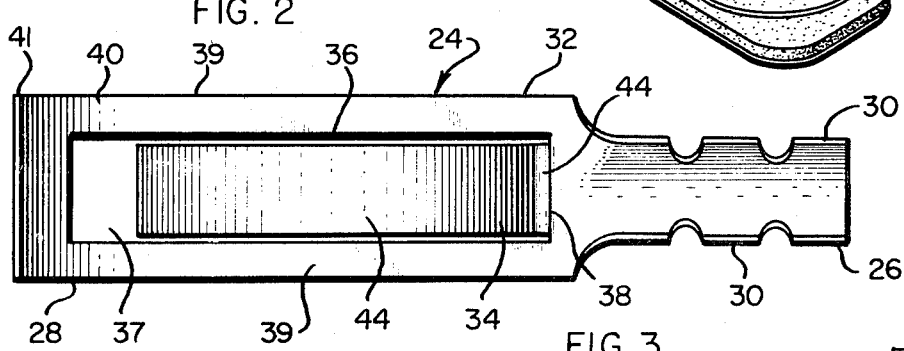
FIG. 2 is a top plan view on an enlarged scale of the terminal.
Figure 3:
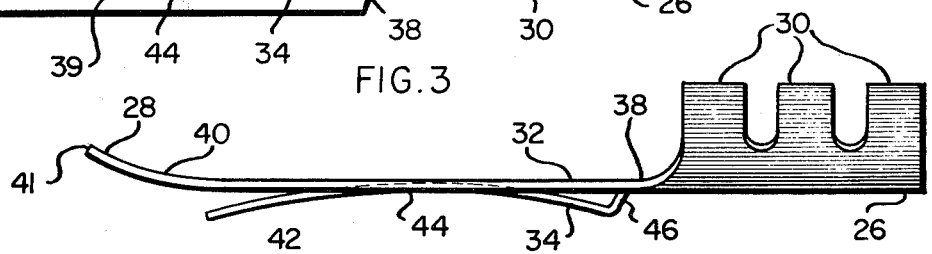
FIG. 3 is a side elevational view of the terminal.
Figure 4:
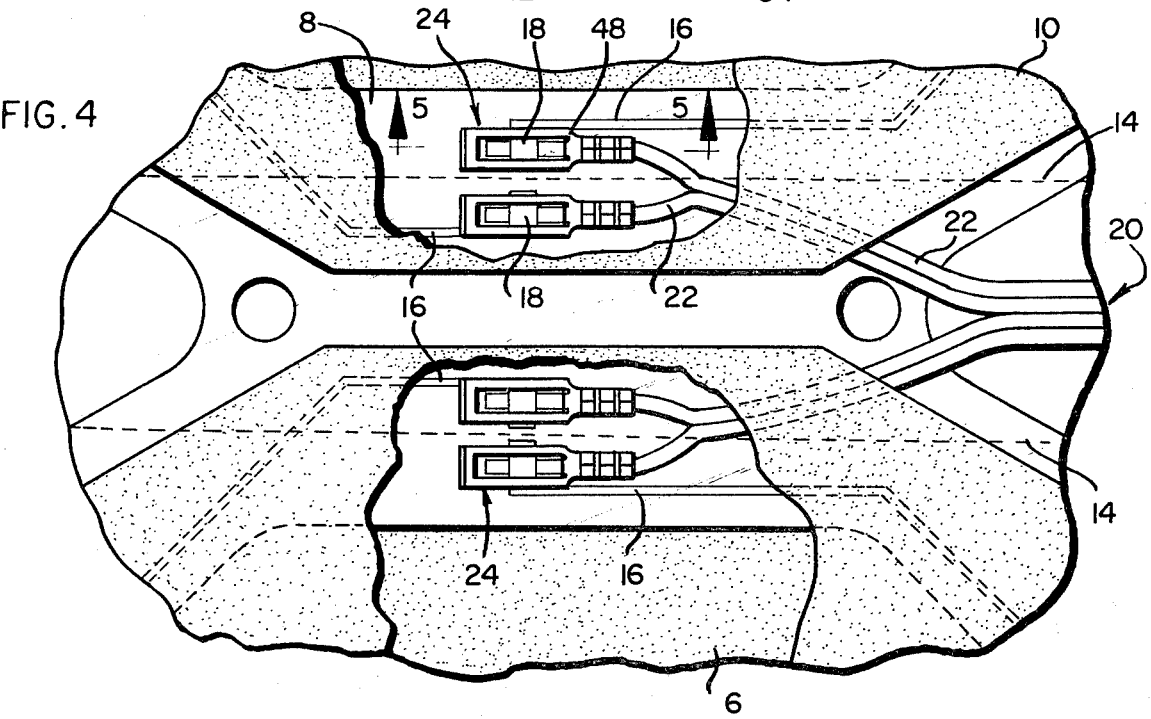
FIG. 4 is a fragmentary top plan view, partially broken away, of the back-pad and showing the terminal embodied therein.
Figure 5:
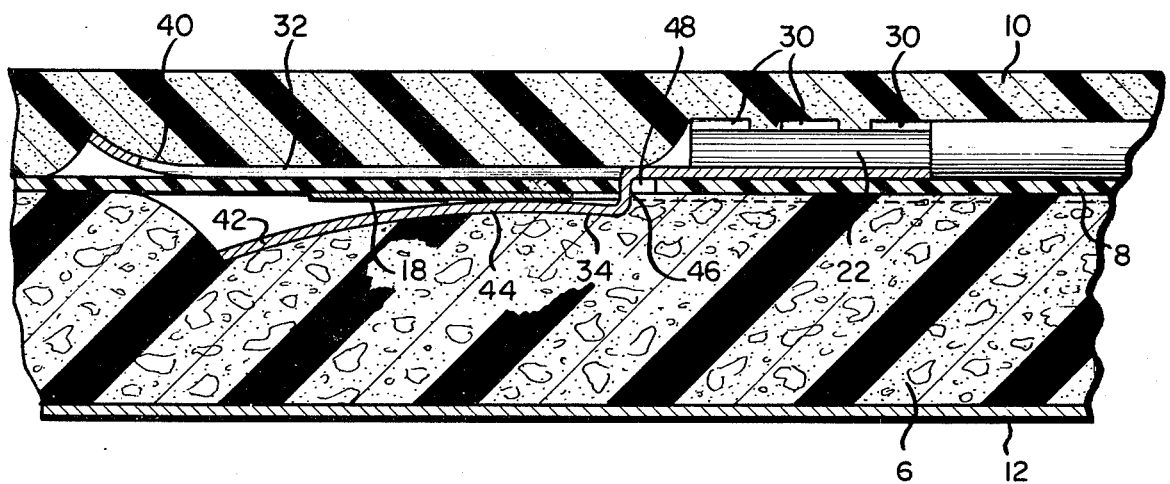
FIG. 5 is a fragmentary sectional view, on an enlarged scale, taken along line 5—5 of FIG. 4.
Figure 6:
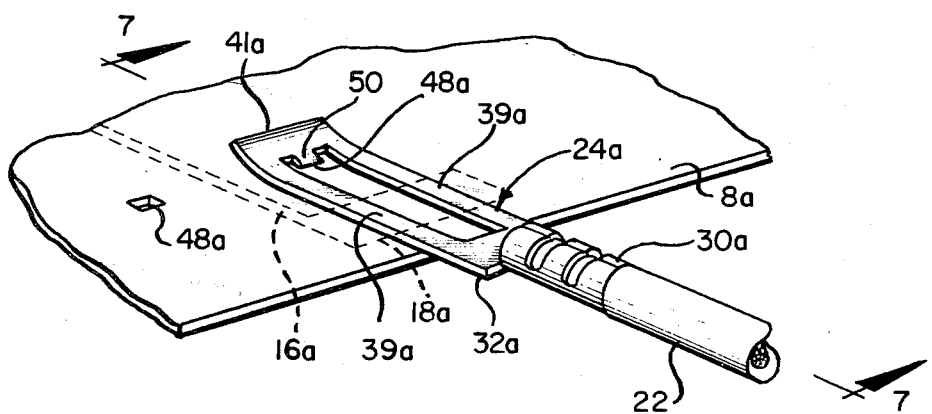
FIG. 6 is a fragmentary perspective view of a modified form of the invention.
Figure 7:
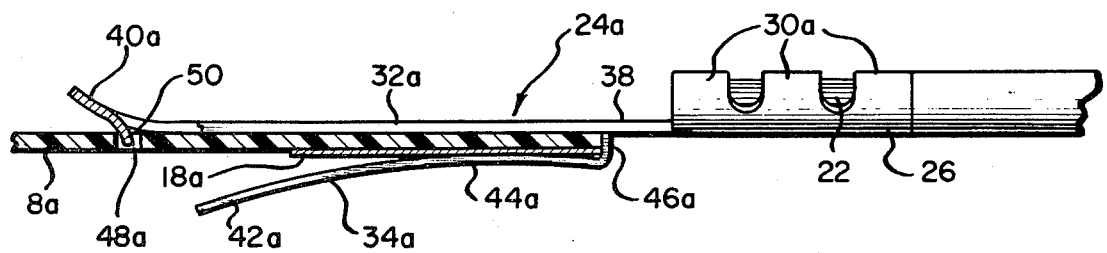
FIG. 7 is a fragmentary section view taken along line 7—7 of FIG. 6.

The wiring harness 20 includes a plurality of insulated wires 22 which are electrically connected to the line segments 18 respectively through terminals 24. Each terminal is a one piece member, preferably formed of a spring brass material and which is intended to clamp onto the dielectric sheet 8. The terminal 24, as shown in FIGS. 2 and 3 has a resiliently conductive body having first and second opposite ends 26, 28, the first end 26 including attaching means for connecting the terminal to one of the wires 22. For this purpose the terminal end 26 has several U-shaped portions 30 which constitute a crimp section. Insulation may be stripped from the wire 22 to expose a bare lead at which the portions 30 may be crimped onto the wire as best shown in FIGS. 5-7.

The terminal body 24 includes, in addition to the crimping means 30, a blade section 32 and a wiper section 34. The wiper section 34 is struck from the balde section 32 along a U-shaped line 36 leaving a generally rectangular opening 37. However, the wiper section 34 remains joined to the blade section 32 along a transverse region 38, which is adjacent to the crimp section 30. The blade section 32 thus has parallel legs 39 which are generally flat from the region 38 toward the free end portion 41 of the blade; however, near its free end the blade section 32 is curved outwardly and upwardly along a segment 40 which projects beyond the tip of the wiper section 34 with the transverse end portion 41 joining the legs 39,39. The wiper section 34 is bent generally in the form of an arc having at its free end a segment 42 which diverges from the segment 40 to provide a mouth that is adapted to receive the dielectric sheet 8 when the terminal is assembled therewith. Segment 40 has a radius of curvature greater than the radius of the arch of the wiper section 34. The central or intermediate portion 44 of the wiper section 34 is thus bowed so that this central portion 44 lies within the perimeter of the opening 37 left as a result of striking out the wiper section 34, and defined by legs 39,39, and end portion 41. Adjacent to the region 38 there is a generally transverse shoulder 46 which forms a sharp angle with each of the wiper and blade sections 34,32. As can be seen the transverse shoulder 46 serves to join the bowed wiper section 34 to the transverse region 38 of the terminal body 24.

Upon assembly of the terminal 24, the wiper section 34 is first inserted into the opening 48 in the dielectric sheet 8. This operation is facilitated by the flared nature of the respective end portions 40 and 42 on the blade and wiper sections. Also, the assembly operation tends to flex the resilient wiper section 34, with the central or intermediate section 44 being engaged with the side of the sheet 8 containing the printed circuit 16 and the terminal line segment 18. Sliding movement of the terminal body 24 with respect to the sheet 8 will continue until the shoulder portion 46 of the wiper section is received within the aperture 48, whereupon said transverse shoulder 46 will abut the aperture edges to prevent further movement. Placement of the aperture 48 is selected in relation to the dimensions of the terminal body 24, such that when this occurs the central or intermediate section 44 will be in engagement with the transverse terminal portion 18. The disposition of shoulder 46 in aperture 48 also serves to provide stop means which prevent inadvertent withdrawal movement of the terminal 24, which could break the electrical contact with the segment 18 of the printed circuit.

Due to the resiliency of the wiper sections 34; and its initial formation to dispose the intermediate portion 44 within the perimeter of opening 37, upon assembly the wiper section 34 is urged against the sheet. Accordingly, the wiper section 34 and the legs 39, 39 apply opposed gripping forces to the sheet 8 on opposite sides thereof. The crimp section 26 also is formed to be flush against the dielectric sheet 8 to maintain a low profile. After the low profile terminals 24 are assembled to the dielectric sheet, the second, relatively thin foam sheet 10 is affixed. The sheet 10, along with the low profile of the terminal 24 serves to provide a back-pad construction that will remain comfortable to the patient, during extended periods of usage.

A modified form of terminal used as an edge connector is shown in FIGS. 6 and 7, and designated 24a wherein like reference numerals followed by "a" identify parts corresponding in structure and function to parts previously described. In this embodiment the dielectric sheet 8a is provided with one or more perforations 48a, each perforation 48a being spaced from but relatively adjacent to a printed conductor line segment 18a. With the terminal 24a, the blade portion segment 40a is provided with a tine 50 which projects through opening 48a and serves to inhibit relative sliding movement of the sheet 8a and the terminal 24a. The inner surface of shoulder 46a abuts the edge of the sheet 8a serving to position the intermediate portion 44a for engagement with segment 18a, and cooperates with tine 50 to assure maintaining of the proper position for the terminals 24a.

The invention is claimed as follows:

1. A terminal for making electrically conductive connection with a printed electrical conductor on one side of a thin flexible sheet of dielectric material, said terminal comprising; a resilient electrically conductive body having first and second opposite ends, said first end having attaching means for connection to an electrical conductor, said body having a blade section and a wiper section, the wiper section being struck from the blade section along a U-shaped line but remaining joined thereto at a region adjacent to said attaching means, said blade section upon the striking of the wiper section therefrom including a pair of substantially parallel, spaced leg portions and an end portion which interconnects the free ends of said leg portions remote from the location of attachment of the wiper section to the blade section, and said end portion cooperating with said leg portions to define an opening in said blade section, said wiper section being bowed and including an intermediate portion disposed in said opening defined in the blade portion and positioned between the spaced leg portions, the free ends of said wiper section and said blade section diverging in the direction toward said second end to facilitate reception of the dielectric sheet therebetween, such that the wiper section is adapted to engage in wiping contact the side of the sheet having the printed conductor thereon, and the blade section is adapted to engage the sheet on the side thereof opposite to said printed conductor, the joining of the free ends of said spaced leg portion by said end portion restricting the flexibility of said blade section, such that upon engagement with said sheet, the wiper section will flex primarily with the intermediate portion of said wiper section engaging the printed conductor or said sheet and the spaced leg portion of the blade section applying opposed gripping forces to the opposite side of said sheet at locations offset laterally from that wherein said wiper section engages said sheet, and means on said body adapted to cooperate with said sheet for inhibiting relative sliding movement of the terminal with respect to said sheet.

2. A terminal according to claim 1 in which said last-named means is a shoulder at the region of juncture of the wiper section and the blade section and forms an angle with each of said wiper and blade sections.

3. A terminal according to claim 1 in which said last-named means is a tine on and projecting from said blade section in a direction toward said wiper section for disposition in an aperture formed in said sheet.

* * * * *